United States Patent
Krijnen et al.

(10) Patent No.: US 12,016,337 B1
(45) Date of Patent: Jun. 25, 2024

(54) SYSTEM FOR MIXING GERMICIDALLY ACTIVE SOLUTIONS, ON-SITE, FOR DAIRY/AGRICULTURAL HYGIENE PURPOSES

(71) Applicant: ACEPTEC, LTD, Ontario (CA)

(72) Inventors: Robertus T Krijnen, Ontario (CA); Michael C. Pawlak, Middleton, WI (US)

(73) Assignee: ACEPTEC, LTD, Thorndale (CA)

( * ) Notice: Subject to any disclaimer, the term of this patent is extended or adjusted under 35 U.S.C. 154(b) by 0 days.

(21) Appl. No.: 18/234,755

(22) Filed: Aug. 16, 2023

(51) Int. Cl.
*A01N 59/00* (2006.01)
*A01J 7/04* (2006.01)

(52) U.S. Cl.
CPC ................. *A01N 59/00* (2013.01); *A01J 7/04* (2013.01)

(58) Field of Classification Search
CPC ........... A01N 59/00; A01N 25/22; A61L 2/22; A61L 2/26; A61L 2202/11; A61L 2202/16; A61L 2209/213; A61L 9/14
See application file for complete search history.

(56) References Cited

U.S. PATENT DOCUMENTS 11,446,618 B1 * 9/2022 Krijnen .................... C11D 3/48

* cited by examiner

*Primary Examiner* — Audrea B Coniglio
(74) *Attorney, Agent, or Firm* — Charles S. Sara; Yanjun Ma; De Witt LLP

(57) ABSTRACT

A system for on-site production of chlorine dioxide and other sanitizing solutions is disclosed which includes an activation chamber to mix concentrated activator and base solutions. The resulting solution from the activation chamber is then mixed with water in a two-stage measurement/mixing vessel to create a ready-to-use cleaning solution. A drainage system is employed to transfer the ready-to-use cleaning solution into a reservoir for on-site use.

18 Claims, 1 Drawing Sheet

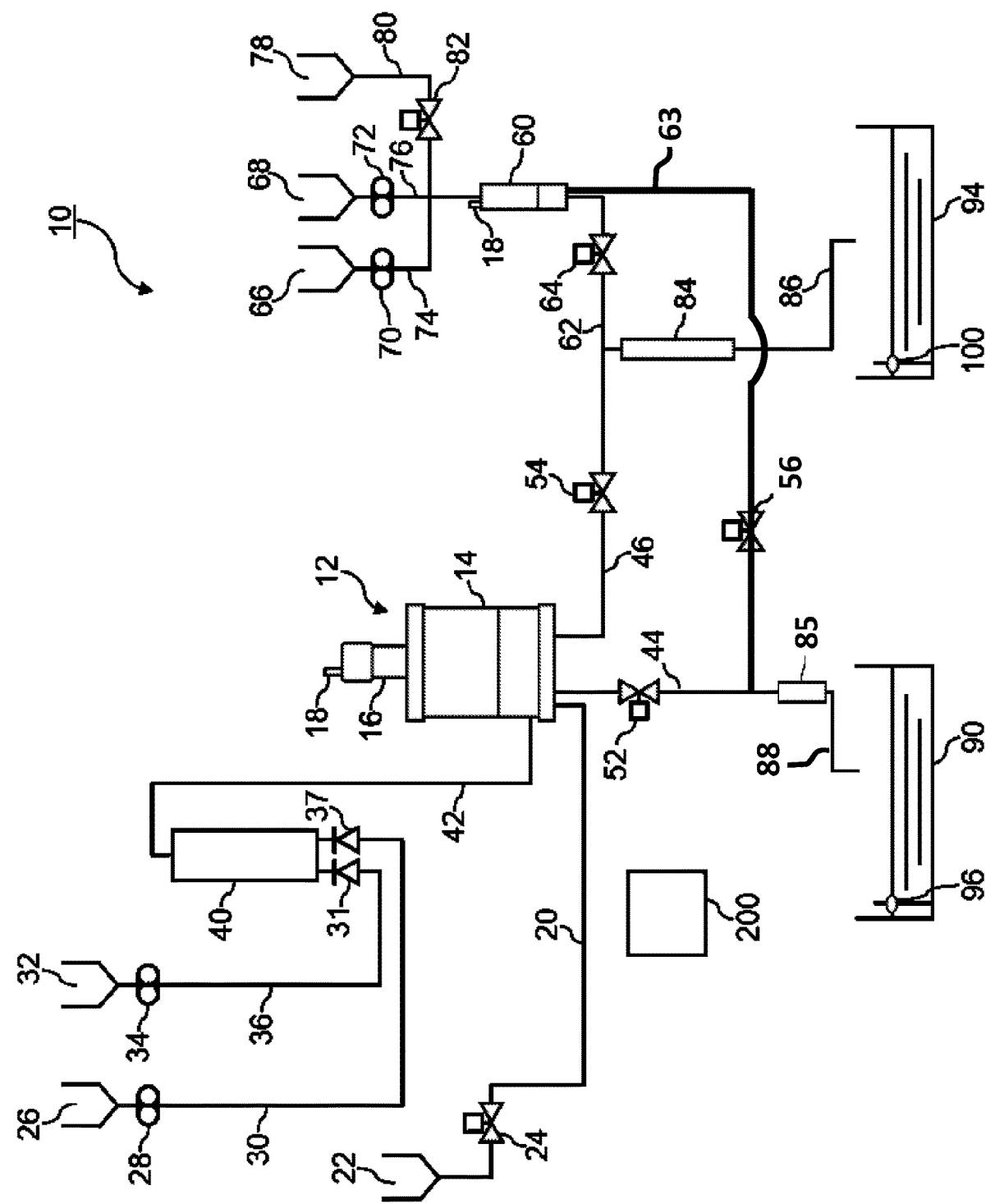

SYSTEM FOR MIXING GERMICIDALLY ACTIVE SOLUTIONS, ON-SITE, FOR DAIRY/AGRICULTURAL HYGIENE PURPOSES

FIELD OF THE INVENTION

The present disclosure relates to systems and methods for generating germicidal compositions on-site, for use in a wide variety of agricultural and non-agricultural settings, including, but not limited to: animal hygiene, e.g. pre-milking, system backflushing and post milking animal hygiene, animal facility hygiene, agricultural food production settings, veterinarian settings, medical settings and/or any setting requiring disinfection using one or more required germicidal active solutions.

BACKGROUND

Mastitis is an inflammation of the mammary gland and udder tissue and is a major endemic disease of milk-producing animals. It usually occurs as an immune response to bacterial invasion of the milk producing glands by variety of bacterial sources present in agricultural/milk harvesting settings. Mastitis is the costliest disease to the dairy industry, estimated at nearly $2 billion dollars annually in the U.S. (Schroeder, 2012).

To overcome this disease, modern milk producing facilities have employed multiple pre-milking and post-milking hygiene practices to clean, disinfect and prophylactically protect an animal from contact with disease causing organisms in its environment, or through the cow-to-cow contact that occurs during the milking process.

In dairy farm milk harvesting facilities, dairy animals are commonly treated with antimicrobial solutions prior to, and/or after the milk harvesting process. These solutions are generally known within the industry as "teat dips." The prior-to-milking solutions are commonly referred to as "pre dips," and the after-milking harvesting solutions are commonly referred to as "post dips." While dairy producers may sometimes use the same product for pre-milking and post-milking disinfection, these solutions generally are developed, produced and sold separately. Each process, pre-milking disinfection and post-milking disinfection, has significant differences in its application, is therefore generally developed and produced separately.

In the pre-milking process, the cleaning and sanitizing of teats before attaching the milking machine is a very important step in preventing bacteria from getting into the teat canal and milk producing glands during the milking process. Environmental organisms such as *Streptococcus uberis*, *Streptococcus dysgalactiae* and the coliforms (*E. coli, Klebsiella* and *Enterobacter*) are in the soil and manure and are commonly found on the teat ends and teat skin surfaces. These contaminants must be cleaned off and the bacteria killed before attaching the milking unit. If they are not, there is always a strong possibility that bacteria could be forced into the teat/milking producing glands during the milking process, resulting in new intermammary infections (IMI's). The common pre-milking teat dip solution elements needed are "fast kill/wide spectrum" germicidal agents and cleaning surfactants in a diluted aqueous solution.

In the post-milking application, the solution of disinfecting agents provides a prophylactic barrier against bacteria entering the milk-producing glands after the milking process. The individual cow teat sphincter muscles remain open for a period after the milking process is completed. Germicidal solutions are applied to the individual teats immediately after the milking cluster is removed from the cow to:

1. Seal the teat and protect against bacteria entering the cow teats from the open sphincter muscle; and
2. Coat the teat with germicidal and skin conditioning agents that will keep the teat skin healthy and free of contagious and infectious disease-causing organisms.

This difference in application requires a substantial difference in the formulation components. The post milking solutions, by the nature of the solution, generally require a higher germicidal content to continue to protect over a longer period after application. The post-dip formulation also requires teat coating and teat skin conditioning agents. These agents are not used in optimum pre-milking formulations.

90+% of the pre- and post-milking formulations fall in the classification of oxidizers as the general source of disinfection properties. Oxidizing agents act by oxidizing the cell membrane of micro-organisms, which results in a loss of structure and leads to cell lysis and death. Chlorine and oxygen are strong oxidizers, so their compounds are primary compounds within this group. Other oxidizing agents used for pre- & post-milking hygiene are: iodines, sodium hypochlorite, peroxides and peracetic acid and chlorine dioxide. These compounds are generally diluted at their place of manufacturing, and additional agents are added to the formulations to aid in cleaning or as skin conditioning agents. It is typical that these products are comprised of 90%+ of water, making the packaging and shipment of these compounds more expensive.

Chlorine dioxide is a chemical compound with the formula $ClO_2$. This yellowish-green gas crystallizes as bright orange crystals at $-59°$ C. As one of several oxides of chlorine, it is a potent and useful oxidizing agent. In that it is produced as a gas, it must be produced on-site due to the instability of the gas produced. Thus, chlorine dioxide gas is not handled in concentrated form, but is almost always handled as a dissolved gas in water in a concentration range of 0.5 to 10 grams per liter. In many countries, such as the United States, chlorine dioxide gas may not be transported at any concentration and is almost always produced at the application site using chlorine dioxide mixing systems/generators, or manually.

Chlorine dioxide based pre/post milking teat disinfectants represent approximately 8-10% of the U.S. teat dip market, with the pre-dip representing approximately 6% and the post dip representing approximately 12% of the market use. This market is dominated by iodine-based products, representing approximately 60% of the market volume. Chlorine dioxide dips have been proven to be extremely effective as both pre and post milking in protocol evaluations created by the National Mastitis Council (NMC), and have been shown to be equal to, or statistically significantly superior in reducing new IMIs in comparison to iodine formulations. Chlorine dioxides have several characteristics that have subjugated the formulations to a lower market share position:

1. The activator/base formulations must be mixed on-site, in the vicinity of use, and lack mixing systems/devices that are accurate, consistent and affordable;
2. The current activator/base formulations are pre-packaged, and used primarily as post dip configurations due to the higher costs of the formulations due to handling and packaging; and
3. The short shelf life of the on-site produced product, particularly post milking formulations, ranges between 12-48 hours, reducing the amount of product that can be pre-blended at one time.

For the purpose of producing chlorine dioxide-based teat dips/disinfection agents, most on-site applications blend pre-packaged activator and base components on farm in a 1:1 ratio. They are prepared in advance of delivery, typically in separate packaging. The low concentrations of precursor products (1-4%) means that most of the weight (96-99%) of the products consists of substantial amounts of inert, non-germicidal active ingredients, such as water, emollients and cleaning agents. This results in the need for larger product storage areas and causes increased packaging, transportation and handling costs. These costs represent over 60% of the manufactured costs of the pre-milking solutions and 40% of the costs of post milking formulas. Typically, pre-milking teat dips contain a lower level of germicidal active ingredients and skin conditioning agent. To that same point, post milking teat dips provide a higher germicidal content along with teat sealants and skin conditioning agents.

The typical shelf life of a chlorine dioxide-based formulation also plays a role in the product's limited use. The stated shelf life of these blended teat/udder hygiene products ranges between 12-48 hours, as compared to over one year for an iodine-based solution. The relative short shelf life of the chlorine dioxide produced solution is caused by two primary factors: 1) the blended solutions are not contained in sealed containers, and are thus susceptible to "gassing off" the chlorine dioxide gas, and 2) the inherent ingredients provided in the pre-packaged activator and base solutions contain non-activating components (e.g. sealing agents, surfactants and emollients) that lower the yields, time-to-use, stability, and germicidal strengths of the pre-mixed solutions.

To avoid the characteristic problems associated with chlorine dioxide use, mixing systems have been developed for use on dairy facilities that may add water to the mixing system to allow more concentrated versions of the activator and base precursor formulations. These systems use various devices to determine the amount of precursor and water to blend within the process. Some embodiments use pneumatic, vacuum-based pumping devices to pump the solutions into a mixing vessel, some use flow meters, some use static venturi-based based systems that are dependent on specified water flows and precursor viscosities, some gravimetric and require sensitive weighing devices to accurately measure a solution. For these reasons, on-site chemical mixing/blending systems have suffered from low sophistication, non-uniform mixing of the targeted chemical mixtures. Due to the high costs for accurate devices to blend singular formulations, such as post dip only, has caused low adoptions rate, leaving chlorine dioxide blending on-site to manual processes.

There are many chlorine dioxide generation reactions. However, not all of these are commercially suitable for on-site or on-farm generation of chlorine dioxide for animal or facility hygiene purposes. These types of generators are high output units typically used for water disinfection, or paper pulp bleaching operations. The following four listed are the most common chlorine dioxide generation methods (Gates, 1998):

Electrochemical: 1) Anode (oxidation): $ClO_2^- \rightarrow ClO_2 + e^-$
2) Cathode (reduction): $2H_2O + 2e^- \rightarrow H_2 + 2OH^-$
1)+2) (combined) $2ClO_2^- + 2H_2O \rightarrow 2ClO_2 + H_2 + 2OH^-$ Acid—Chlorite: The mixture of an acid activator (any type) with sodium chlorite. Mixing sodium chlorite solution with an acid solution, both stable as precursors, produces short-lived acidified sodium chlorite (ASC) which has potent decontaminating properties. Upon mixing the main active ingredient, hypochlorous acid is produced in equilibrium with the chlorite anion. ASC is used for sanitation of the hard surfaces and surfaces encountering food, and as a wash or rinse for a variety of foods, including red meat, poultry, seafood, fruits and vegetables. Treated properly the oxi-chlorine compounds are unstable when properly prepared, there should be no measurable residue on food. ASC also is used as a teat dip for control of mastitis in dairy cattle.

Chlorine-Chlorite: $CL_2 + H_2 \rightarrow HOCL + HCL$ (Then refer to three chemical reactions below)

Three Chemical: $2NaClO_2 + HOCL + HCL \rightarrow 2ClO_2 + 2NaCl + H_2O$

SUMMARY

The present disclosure relates to liquid compositions and methods of using the liquid precursor compounds for the generation of, but not limited to, the production of chlorine dioxide sanitizing solutions and cleaners, produced on-site, in proximity to the point-of-use.

In one embodiment, the present disclosure is directed to an on-site system for producing sanitizing and germicidal solutions and cleaners. Specifically, the present disclosure is directed to an on-site system 10 for producing ready-to-use product solutions.

The system 10 comprises a plurality of precursor source vessels 26, 32, wherein each precursor source vessel contains a distinct precursor solution, and each precursor source vessel is connected to one of a plurality of pumps 28, 34 for pumping the precursor solution into an activation chamber 40.

The activation chamber 40 receives and mixes each of the precursor solutions to make a first solution, wherein the first solution subsequently enters a first measurement/mixing vessel 12. The activation chamber 40 is primed to be filled with the precursor solutions before the system is activated. When the system is activated, each of the precursor solutions are added from the plurality of precursor source vessels 26, 32 to the activation chamber 40 to push the first solution out of the activation chamber 40 into the first measurement/mixing vessel 12. Preferably, activation chamber 40 is under backpressure.

In certain versions, the plurality of precursor source vessels 26, 32 comprises an activator source vessel 26 and a base source vessel 32 for dispensing an activator and a base into the activation chamber 40. In certain versions, the activator is an acid. The base is a concentrated solution of sodium chlorite. The resulting first solution comprises chlorine dioxide.

The first measurement/mixing vessel 12 mixes water with the first solution to make the ready-to-use product solution. The first measurement/mixing vessel 12 comprises a first chamber measurement vessel 14 that is pre-filled with water before the system is activated; a second chamber measurement vessel 16 for measuring the incoming first solution; and a plurality of system drain switches 52, 54 for releasing the ready-to-use product solution from the first measurement/mixing vessel 12. The first measurement/mixing vessel 12 further comprises a channel tube 20 connected to an incoming water source 22 wherein the channel tube 20 includes a water solenoid switch 24 for measuring the flow of water into the first chamber measurement vessel. The first measurement/mixing vessel 12 further comprises an ultrasonic fill-level sensor 18 for accurately determining and measuring the quantity of water in the first chamber measurement vessel 14.

The system 10 further comprises a second measurement/mixing vessel 60 for receiving water from a water source 78 and additives from at least one auxiliary source vessel 66, 68 for providing a supplementary solution to the ready-to-use product solution. In some embodiments, the additives are selected from the group consisting of color additives, emollients, and sealing agent additives.

The system 10 further comprises static mixers 84 and/or 85 for blending the ready-to-use product solution from the first measurement/mixing vessel 12 and/or the supplementary solution from the second measurement/mixing vessel 60.

The system 10 further comprises a plurality of reservoirs 90, 94 for collecting the ready-to-use product solution. Each reservoir 90, 94 comprises a float switch 96, 100 for measuring current level of the ready-to-use product solution in the reservoir, wherein the float switch 96, 100 is in communication with a programmable logic controller 200 to activate the system when the ready-to-use product solution level is low and deactivate the system when the ready-to-use product solution level is full.

Advantageously, the system disclosed herein is designed to maximize the concentration levels of the sanitizing solutions and reduce chemicals needed. For example, by mixing concentrated activator and base in the activation chamber without adding additional water, the resulting concentration of chlorine dioxide is increased. For making the ready-to-use product solution at the same ppm level, less activator and base are needed compared to systems without the activation chamber.

The system is also designed to increase the accuracy, repeatability and safety of the system, and use of on-site blended formulations. The system allows a facility to build/blend formulations specific to the application, without having to overproduce and lose efficacy and influence the product's shelf life.

In some embodiments, the system can blend on-site, with the use of proprietary precursors and on-site water formulations, specific to the pre-milking cleaning and sanitizing application. In some embodiments, the system can blend on-site, with the use of proprietary precursors and on-site water formulations, specific to the post-milking cleaning and sanitizing application. In some embodiments, the system can create chlorine dioxide formulations either for, but not limited to, pre-milking hygiene practices, post-milking hygiene practices and equipment sanitizations. In some embodiments, each operation is kept track of in a batch format, identifying the date & time of the process, the individual batch size and volumes of each precursor component, and water, along with the tracking of the batch's individual chemical signature identified by its pH, and oxidation reduction potential (ORP) values.

Teat dips produced from the system disclosed herein can be applied and used without further mixing, storage or processing, in a range of applications that the ready-to-use (RTU) product that has been created. They may be applied, but are not limited to, being used through a pre-milking teat scrubber mechanism. They may be sprayed, dipped or foamed on to a cow's teats, specific to the formulation created.

In some embodiments, the system can produce products used for, but not limited to, hoof hygiene, calf hygiene, animal/facility hygiene, water treatment, vegetable and fruit washing. By reducing the costs of producing chlorine dioxide on-site, a facility dramatically lowers their overall costs of not only producing the chlorine dioxide at a lower cost, but the costs of packaging, shipping, handling and storage of chemicals, and the costs of keeping their animals and/or products at a higher quality level.

The objects and advantages of the disclosure will appear more fully from the following detailed description of the preferred embodiment of the disclosure made in conjunction with the accompanying drawings.

BRIEF DESCRIPTION OF THE DRAWINGS

FIG. 1 is a flowchart illustrating the component features of the system disclosed herein.

DETAILED DESCRIPTION

The system of the present disclosure is capable of producing a multitude of cleaning products for use on-site. While the on-site system has application in many venues, from the farm industry to automotive or factory settings, the system herein will be specifically described with respect to cleaning products for use on a dairy farm.

Reference is made to FIG. 1, which is a flowchart, illustrating a representative system 10 of the present disclosure. As illustrated in FIG. 1, and for exemplary purposes only, the system 10 is used for producing two separate formulas: formula 1 is a chlorine dioxide sanitizing solution and formula 2 is a chlorine dioxide sanitizing solution comprising additives such as emollients and color additives. For purposes of the presently described disclosure, formulas 1 and 2 are known as teat dips. Formula 1 is a pre-dip formula described above as a "prior-to-milking" teat cleaning solution. Formula 2 is a post-dip formula described above as an "after-milking harvesting solution" for post-milking hygiene and disinfection practices.

Precursor Source Vessels

The system 10 provides an activator source vessel 26 for providing activators to the activation chamber 40. The activator is generally a concentrated acid-based aqueous solution that is formulated to activate a base. As illustrated in FIG. 1, the activator source vessel 26 feeds into an inlet channel 30 for dispensing the activator into the activation chamber 40. The activator source vessel 26 is provided with a pump 28, which measures the required amount of activator to be added to the activation chamber 40. A variety of pumps, known to the art, can be used for this purpose. Preferably, the pump is a peristaltic pump, a type of positive displacement pump used for pumping a variety of fluids.

Further, there is a base source vessel 32 for providing a base solution. The base is generally a concentrated solution of sodium chlorite. The base source vessel 32 feeds into an inlet channel 36 for dispensing the base into the activation chamber 40. The base source vessel 32 is provided with a peristaltic pump 34 for measuring the required amount of base to be added to the activation chamber 40.

The activator source vessel 26 and the base source vessel 32 comprise the formula of ingredients depending on the requirements. For example, the activator source vessel 26 and the base source vessel 32 can include the activating formula necessary for producing the pre-teat dip formula 1 and the post-teat dip formula 2 as described above.

Activation Chamber

The on-site system 10 comprises an activation chamber 40 that receives and mixes the activator from the activator source vessel 26 and the base from the base source vessel 32. The activator and base enter through the one-way valves 31, 37 into the bottom of the activation chamber 40. Before the on-site system 10 is activated to produce formula 1 or formula 2, the activation chamber 40 is primed to be filled with the activator and base. When the on-site system is activated, activator and base are added from the precursor source vessels 26, 32 to the activation chamber 40 to push the resulting chlorine dioxide solution out of the top of the activator chamber 40 to enter the bottom of the two-stage measurement/mixing vessel 12 via the channel 42.

The concentrated activator and base solutions from the precursor source vessels 26, 32 are mixed in the activation chamber 40 without adding additional water. This increases yields of chlorine dioxide due to the increased likelihood of the activator and base molecules bumping into each other. The activation chamber 40 is under backpressure, which also increases the likelihood of the activator and base molecules bumping into each other, and meanwhile decreases the loss of chlorine dioxide to atmosphere by decreasing the overall vapor pressure of the solution. The design of the activation chamber 40 in the system 10 increases the ppm level, oxidation reduction potential (ORP) level, and pH of the ready-to-use product solution. In one example, the pH of the ready-to-use product solution at low ppm levels (70-100 ppm) is increased from about 2-3 to about 5-6. For making the ready-to-use product solution at the same ppm level, less precursor chemicals are needed. For example, 50%-75% less activator and base are needed to make chlorine dioxide cleaning products at the same ppm level. The concentration of the activator and base solutions stored in the source vessels can be reduced from 0.4% to 0.07%.

Single Two-Stage Measurement/Mixing Vessel

The on-site system 10 includes a first measurement/mixing vessel 12 for mixing water with the chlorine dioxide solution from the activation chamber 40. As illustrated in FIG. 1, the measurement/mixing vessel 12 is a single two-stage measurement vessel having a first lower chamber measurement vessel 14 and a second upper chamber measurement vessel 16. The chlorine dioxide solution from the activation chamber 40 enters the bottom of the lower chamber measurement vessel 14. Before the on-site system 10 is activated to produce formula 1 or formula 2, the lower chamber measurement vessel 14 is pre-filled with water, such that chlorine dioxide formed in the primed activation chamber 40 off gases to the lower chamber measurement vessel 14 to be dissolved in the water. This design reduces loss of chlorine dioxide to the atmosphere and thus increases the concentration of chlorine dioxide in the ready-to-use product solution. When the on-site system is activated, solutions from the activation chamber 40 entering the measurement/mixing vessel 12 are measured by increment indicated by the upper chamber measurement vessel 16 until reaching a required amount.

The measurement/mixing vessel 12 is further provided with a channel tube 20 for providing potable water from a water source 22 to the lower chamber measurement vessel 14. The measurement/mixing vessel 12 is further equipped with an ultrasonic level sensor 18, known to the art, for measuring the volume of water entering the measurement/mixing vessel 12. The ultrasonic sensor 18 is used to determine and measure the water level in the lower vessel 14 by providing instructions to an in-coming water solenoid switch 24.

The measurement/mixing vessel 12 is further provided with drain tubes 44, 46 for removing the resulting solution from the measurement/mixing vessel 12. Each of the drain tubes 44, 46 include a drain valve 52, 54.

The resulting solution is allowed to drain through line 44, via valve 52, into a static mixer 85, where, in certain embodiments, the solution from vessel 12 may be combined with the solution from the vessel 60, mixed together, and ultimately drained from the static mixer 85 into line tube 88.

Single-Stage Measurement/Mixing Vessel

For certain applications, particularly a post-dip formula which may require additional ingredients, a secondary independent single-stage measurement/mixing vessel 60 is provided. In this manner, the cleaning solution from the vessel 12 is further processed by admixture with the solution exiting vessel 60 via drain tube 62. A regulatory drain valve 64 is provided in drain tube 62 to monitor the flow of formula. The purpose of vessel 60 is to allow the addition of other ingredients, such as emollients, sealing agents, and color formulas to the final formula. Source vessels 66, 68 provide the necessary ingredients via the actions of peristaltic pumps 70, 72 measuring the liquid ingredients into the vessel 60 by way of line tubes 74, 76. Water is provided from water source 78 via line tube 80. The quantity of water is measured by valve 82. Once the appropriate quantities of solutions from vessels 66, 68 and water from source 78 are combined in vessel 60, the resulting solution is allowed to drain through line 62, via valve 64, into a static mixer 84, where the solution from vessel 60 is combined with the solution from the vessel 12 and mixed together and ultimately drained from the static mixer 84 into line tube 86. In certain embodiments, the resulting solution is allowed to drain through line 63, via valve 65, into another static mixer 85, where the solution from vessel 60 is combined with the solution from the vessel 12 and mixed together and ultimately drained from the static mixer 85 into line tube 88.

Reservoirs

Each resulting "ready-to-use" product (RTU solution) is stored in an independent reservoir that is in communication with the system's remote controller 200. The RTU solution storage system consists of storage vessels ranging in size from 50 liters to 1,000 liters, determined by the size/RTU solution storage requirements of the individual facility. Additional storage vessels may be used.

The formula resulting from the measurement/mixing vessel 12 drains via drain tube 44 to optionally mix with the supplementary solution from the measurement/mixing vessel 60 and ultimately drains to reservoir 90 via drain tube 88 to be used as formula 1. The formula resulting from the measurement/mixing vessel 12 drains via drain tube 46 to further mix with the supplementary solution from the measurement/mixing vessel 60 and ultimately drains to reservoir 94 via drain tube 86 to be used as formula 2. When a float switch 96, 100 inside each of the reservoirs 90, 94 detects a low level for any of these solution products, an electronic message is passed to controller 200 to activate the corresponding system to top up the corresponding reservoirs 90, 94 by mixing the respective product following a pre-programmed recipe. The float switch 96, 100 is in communication with the controller 200. Float switches and liquid level control sensors and relays are known to the industry. A representative example of a sensor for use in this operation is a Knight Float Switch 951-231 (Inlayout, LLC, New Orleans, LA).

As described above, the system 10 may make the following two products:

Formula 1: pre-teat dip formula utilizing the activator solution from source vessel 26, the base solution from source vessel 32, and water from water source 22;

Formula 2: post-teat dip formula utilizing the activator solution from source vessel 26, the base solution from source vessel 32, water from water source 22, a color formula (if desired) from source vessel 66, emollient solution from source vessel 68, and water from water source 78.

Thus, the pre- and post-dip formulas can use many of the same ingredients, according to the customer's specifications. Both the pre- and post-dip formulas can include emollients, color and foam.

Programmable Logic Controller Control Panel

The system 10 includes a programmable logic controller 200, which is capable of operating water fill valves supplying the measurement/mixing vessels 12, 60 with water and operating the drain valves 52, 54, 64, 65 to empty the measurement/mixing vessels 12, 60 into the reservoirs 90, 94. In addition, the controller 200 is capable of accurately releasing small amounts of precursors from source vessels 26, 32 into the activation chamber 40 and small amounts of additives from source vessels 66, 68 into the measurement/mixing vessel 60 using the peristaltic pumps 28, 34, 70, 72 associated with each source vessel. The controller 200 is known to the industry for similar operations. A representative example of a controller 200 is a programmable logic controller made by Siemens SIMATIC S7-1200, with SM1231A1 ANALOG CONTROLLER (Germany).

The system has an operating temperature range from −25 to +55° C., with the same precision and reliability, making the unit suitable for enclosed outdoor use and agricultural applications.

A second communications port in the controller 200 (not illustrated) can be provided to enable SMS text messages to be sent to mobile phones, e-mails to PCs and faxes in addition to using remote maintenance functions via modem. The control unit can also communicate with other controllers or peripheral components. Security can be ensured by three levels of password protection to prevent unauthorized access to the program and process variable data.

Operation

Referring to FIG. 1, when the system 10 is turned on, the lower chamber vessel 14 of the first measurement/mixing vessel 12 is filled with water to the rim just inside the upper chamber vessel 16, and the activation chamber 40 is primed to be filled with activator and base from the source vessels 26, 32.

All components of the system are in communication with the controller 200. When the controller 200 receives a low signal (closed signal) from one of the float switch level controls 96, 100, the controller 200 thereby activates the pumps 28, 34 to add activator and base from the source vessels 26, 32 to the bottom of the activation chamber 40. The added activator and base then push the solution out of the top of the activation chamber 40 into the bottom of the two-stage measurement/mixing vessel 12 to mix with water. The amount of solution from the activation chamber 40 entering the vessel 12 is measured by increment indicated by the upper chamber measurement vessel 16. When a predetermined amount of solution from the activation chamber 40 is added to the vessel 12, the controller 200 signals to turn off the pumps 28, 34.

For a formula 1 that does not require supplementary solutions, the solution from the first measurement/mixing vessel 12 is directly drained to the RTU reservoir 90. For a formula 1 that requires supplementary solutions, the controller 200 also activates the valve 82 to fill the measurement/mixing vessel 60 with a predetermined amount of water, and activates the pumps 70, 72 to add color additive and/or emollients as needed to mix with water in the measurement/mixing vessel 60. Solutions from the measurement/mixing vessels 12, 60 are drained simultaneously through the static mixer 85 into the RTU reservoir 90. For formula 2 that requires supplementary solutions, the controller 200 also activates the valve 82 to fill the measurement/mixing vessel 60 with a predetermined amount of water, and activates the pumps 70, 72 to add color additive and/or emollients as needed to mix with water in the measurement/mixing vessel 60. Solutions from the measurement/mixing vessels 12, 60 are drained simultaneously through the static mixer 84 into the RTU reservoir 94.

When the reservoirs 90, 94 reach the full level, the flow switch level controls 96, 100 send a signal to the controller 200 to deactivate the system, and the two-stage measurement/mixing vessel 12 is filled with water and waits for the next cycle.

If any other input signal from a remaining level control sensor becomes active, the signal is ignored until the first fill sequence is completed. In other words, the system ignores the other input signals, and produces ready-to-use (RTU) products on a "First come, first serve" basis. For example, if the system gets a signal from the float switch level control 96, the system continues to keep the signal cycling until the float switch level control 96 indicates the reservoir 90 is filled. Then, the system 10 starts based upon the next in-line signal.

The system 10 can be used to make a predetermined batch volume of the ready-to-use product solution. For example, to make a 10 L batch of formula 1 without supplementary solutions, the lower chamber vessel 14 of the first measurement/mixing vessel 12 is pre-filled with 5 L water. After adding a predetermined volume of solutions from the activation chamber 40 to the first measurement/mixing vessel 12, the resulting solution is drained to reservoir 90. Then the first measurement/mixing vessel 12 is rinsed with the remaining volume of water and drains to the reservoir 90 to make a 10 L batch. To make a 10 L batch of formula 2 with supplementary solutions comprising additives such as emollients and color additives, the second mixing vessel 60 is filled with 1 L water from water source 78 and predetermined volumes of additives from source vessels 66, 68. Solutions from the vessels 12 and 60 are drained simultaneously to the reservoir 94 through the static mixer 84. Then, the mixing vessel 60 is rinsed with 3 L of water, and the mixing vessel 12 is rinsed with the remaining volume of water, and both are drained to the reservoir 94 to make a 10 L batch.

Germicidal Composition

The present disclosure is not limited to the production of a germicidal active solution, such as chlorine dioxide ($ClO_2$). The produced solution is not limited to a specific PPM, ORP or pH range, or a particular disinfectant use. For example, in some embodiments, the RTU solution is used for pre and/or post milking hygiene applications. In some embodiments, the produced solution is used for premise hygiene purposes, such as sand/bedding cleaning and disinfection. In some embodiments, the produced solution is used for water treatment and purification. Each of these formulations are designed to meet the specific requirements of the RTU solutions application.

Chlorine dioxide formulations, produced through acidified chlorite procedures, vary in strength and efficacy based upon the strength of an acid, and the additional agents within a formulation. The RTU solution can be produced at PPM levels between 10 PPM and 5,000 PPM $ClO_2$. The RTU solution is not limited to a particular use or function.

Documentation has shown that the RTU formula can operate effectively with $ClO_2$ in a range of pH levels (e.g., pH levels between 4-10 range). The present disclosure is not limited to a particular concentration of sodium chlorite precursor or acid activator precursor, nor is it limited to a specific activator formulation. In some embodiments, the sodium chlorite is an aqueous solution in concentrations of greater than 5%.

For the purpose of generating chlorine dioxide based germicidal and hygiene treatment solutions, the precursors may contain, but not be limited to, a concentrated acidic based formulation (activator) and a concentrated aqueous based sodium chlorite (base) formulation. The activator/base formulations are mixed on site in concentrated versions in the activation chamber to produce chlorine dioxide-based treatment solutions.

Chlorine dioxide can be used as oxidizer or disinfectant. It is a very strong oxidizer, and it effectively kills pathogenic microorganisms such as fungi, bacteria and viruses. It also prevents and removes biofilms. As a disinfectant, it is mainly used in liquid form. Chlorine dioxide can also be used against anthrax because it is effective against spore-forming bacteria. As an oxidizer, chlorine dioxide is very selective. It has this ability due to unique one-electron exchange mechanisms. Chlorine dioxide attacks the electron-rich centers of organic molecules. One electron is transferred, and chlorine dioxide is reduced to chlorite ($ClO_2^-$).

The strength of the activated chlorine dioxide solution can be measured in PPM and Oxidation Reduction Potential (ORP). A solution's ORP value is measured in millivolts (mV), providing a standardized approach to identifying a solution's germicidal value.

Producing chlorine dioxide solutions, with higher yield conversions between the activator precursors and the base precursors, thus achieving higher ORP and PPM readings, is an important part of the design of the system hardware and precursor development. The activator and base precursors are firstly mixed in the activation chamber and the resulting chlorine dioxide is further diluted on-site with an on-site water source to meet individual RTU formulation needs. Knowing that those formulations are influenced by non-activating components allows the formulations to be produced in an optimized fashion. The formulation components and their sequence of mixture also affect the solutions germicidal capability, measured in both PPM and ORP readings, thus the precursor formulations, and the sequence in which they are mixed, play an important role in a product's efficacy, stability and application specific requirements.

Representative System for a Milking Operation

As an example, a pre-milking hygiene treatment solution may be produced in the system at PPM levels of chlorine dioxide in the 100-500 PPM range, while a post-milking treatment formulation may be produced at a range of 500-1,000 PPM. A water treatment solution may be produced at 10 PPM. The system of the present disclosure can automatically produce the complete range of treatment solutions, as determined by the individual facility requirements.

Thus, the system has the ability to produce a range of treatment solutions that are pre-defined by the requirements of the treatment's individual application, as an example, a pre-milking chlorine dioxide treatment used through milking teat scrubber known to the art, or a treatment solution used for post-milking teat protection application. Through the system, and the pre-determined precursor formulations, the system can produce treatment solutions individually tailored to a facility's requirements.

Individual precursor formulations are developed to use the system for the on-site production of the individual treatment solutions. The system has the ability to vary the individual treatment formulations to be specific to the requirements of the individual on-site needs; as an example the system can be set to vary the individual PPM levels or the pre-milking cleaning and sanitizing solutions between 100-500 PPM, and vary the individual post-milking treatment solutions between 500-1000 PPM by adjusting the peristaltic pump run times and speeds, and the measurement vessel liquid level sensors to the desired levels. This allows each system to be set to the individual requirements of the site and environment that it operates in.

In the foregoing description, certain terms have been used for brevity, clarity, and understanding. No unnecessary limitations are to be inferred therefrom beyond the requirement of the prior art because such terms are used for descriptive purposes and are intended to be broadly construed. The different configurations and systems described herein may be used alone or in combination with other configurations and systems. It is to be expected that various equivalents, alternatives and modifications are possible within the scope of the foregoing description.

Any version of any component of the disclosure may be used with any other component of the disclosure. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

As used herein, the term "or" is an inclusive "or" operator and is equivalent to the term "and/or" unless the context clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The systems of the present disclosure can comprise, consist of, or consist essentially of the essential elements and limitations described herein, as well as any additional or optional steps, ingredients, components, or limitations described herein or otherwise useful in the art. The disclosure provided herein may suitably be practiced in the absence of any element which is not specifically disclosed herein.

While this disclosure may be embodied in many forms, what is described in detail herein is a specific preferred embodiment. The present disclosure is an exemplification of the principles of the disclosure and is not intended to limit the disclosure to the particular embodiments illustrated. It is to be understood that this disclosure is not limited to the particular examples, process steps, and materials disclosed herein as such process steps and materials may vary somewhat. It is also understood that the terminology used herein is used for the purpose of describing particular embodiments only and is not intended to be limiting since the scope of the present disclosure will be limited to only the appended claims and equivalents thereof.

BIBLIOGRAPHY

Gates, Don PhD., (1998) The Chlorine Dioxide Handbook, American Water Works Association.
Schroeder (2012) Bovine Mastitis and Milking Management, North Dakota State University, Fargo, North Dakota.
Suslow, Trevor, University of California, Davis, "Post Harvest Quality and Safety from Seed to Shelf.

What is claimed is:

1. An on-site system for producing ready-to-use product solutions, comprising:
    (a) a plurality of precursor source vessels wherein each precursor source vessel contains a distinct precursor solution, and each precursor source vessel is connected to one of a plurality of pumps for pumping the precursor solution into an activation chamber;
    (b) the activation chamber receiving and mixing each of the precursor solution to make a first solution, wherein the first solution subsequently enters a first measurement/mixing vessel;
    (c) the first measurement/mixing vessel for mixing water with the first solution to make the ready-to-use product solution, comprising:
        i. a first chamber measurement vessel pre-filled with water;
        ii. a second chamber measurement vessel for measuring the incoming first solution; and
        iii. a plurality of system drain switches for releasing the ready-to-use product solution from the first measurement/mixing vessel; and
    (d) a plurality of reservoirs for collecting the ready-to-use product solution.

2. The system of claim 1, wherein the ready-to-use product solution is a cleaning or germicidal solution.

3. The system of claim 1, wherein the ready-to-use product solution comprises chlorine dioxide.

4. The system of claim 1, wherein the ready-to-use product solutions are selected from the group consisting of pre-milking teat disinfectants, post-milking teat disinfectants, hoof hygiene disinfectants, calf hygiene disinfectants, animal/facility hygiene disinfectants, water treatment solutions, and vegetable and fruit washing solutions.

5. The system of claim 1, wherein the plurality of precursor source vessels comprises an activator source vessel and a base source vessel for dispensing an activator and a base into the activation chamber.

6. The system of claim 5, wherein the activator is an acid.

7. The system of claim 5, wherein the base is a concentrated solution of sodium chlorite.

8. The system of claim 1, wherein the first solution comprises chlorine dioxide.

9. The system of claim 1, wherein the pumps are peristaltic pumps.

10. The system of claim 1, wherein the activation chamber is primed to be filled with the precursor solutions before the system is activated.

11. The system of claim 1, wherein the activation chamber is under back pressure.

12. The system of claim 1, wherein the first measurement/mixing vessel further comprises a channel tube connected to an incoming water source wherein the channel tube includes a water solenoid switch for measuring the flow of water into the first chamber measurement vessel.

13. The system of claim 1, wherein the first measurement/mixing vessel further comprises an ultrasonic fill-level sensor for accurately determining and measuring the quantity of water in the first chamber measurement vessel.

14. The system of claim 1, further comprising a second measurement/mixing vessel for receiving water from a water source and additives from at least one auxiliary source vessel for providing a supplementary solution to the ready-to-use product solution.

15. The system of claim 14, wherein the additives are selected from the group consisting of color additives, emollients, and sealing agent additives.

16. The system of claim 14, further comprising at least one static mixer for blending the ready-to-use product solution from the first measurement/mixing vessel and the supplementary solution from the second measurement/mixing vessel.

17. The system of claim 1, wherein each reservoir comprises a float switch for measuring current level of the ready-to-use product solution in the reservoir, wherein the float switch is in communication with a programmable logic controller to activate or deactivate the system.

18. An on-site system for producing ready-to-use product solutions, comprising:
    (a) a plurality of precursor source vessels comprising an activator source vessel containing an activator and a base source vessel containing a base, wherein each precursor source vessel is connected to one of a plurality of pumps for pumping the activator and base into an activation chamber;
    (b) the activation chamber receiving and mixing the activator and base to make a first solution, wherein the activation chamber is primed to be filled with the activator and base before the system is activated, and wherein the first solution subsequently enters a first measurement/mixing vessel;
    (c) the first measurement/mixing vessel for mixing water with the first solution to make the ready-to-use product solution, comprising:
        i. a first chamber measurement vessel pre-filled with water;
        ii. a second chamber measurement vessel for measuring the incoming first solution; and
        iii. a plurality of system drain switches for releasing the ready-to-use product solution from the first measurement/mixing vessel;
    (d) a second measurement/mixing vessel for receiving water from a water source and additives from at least one auxiliary source vessel for providing a supplementary solution to the ready-to-use product solution;
    (e) at least one static mixer for blending the ready-to-use product solution from the first measurement/mixing vessel and the supplementary solution from the second measurement/mixing vessel; and
    (e) a plurality of reservoirs for collecting the ready-to-use product solution, wherein each reservoir comprises a float switch for measuring current level of the ready-to-use product solution in the reservoir, wherein the float switch is in communication with a programmable logic controller to activate or deactivate the system.

* * * * *